United States Patent [19]

Yokoyama et al.

[11] Patent Number: 4,742,165

[45] Date of Patent: May 3, 1988

[54] 2-PIPERAZINOPYRIMIDINE DERIVATIVES

[75] Inventors: Keiichi Yokoyama, Iwakuni; Tatsuyoshi Ishida; Shigeru Isayama, both of Ohtake; Kohji Kato, Yamaguchi; Takumi Kitahara, Ohtake; Yoshiaki Furuya, Iwakuni, all of Japan

[73] Assignee: Mitsui Petrochemical Industries, Ltd., Tokyo, Japan

[21] Appl. No.: 865,566

[22] PCT Filed: Sep. 7, 1985

[86] PCT No.: PCT/JP85/00500

§ 371 Date: May 2, 1986

§ 102(e) Date: May 2, 1986

[87] PCT Pub. No.: WO86/01798

PCT Pub. Date: Mar. 27, 1986

[30] Foreign Application Priority Data

Sep. 7, 1984 [JP] Japan .................. 59-186542

[51] Int. Cl.$^4$ .................. C07D 239/84; C07D 239/70; C07D 471/04; C07D 487/04

[52] U.S. Cl. .................. 540/205; 540/460; 540/502; 544/253; 544/254; 544/279; 544/280; 71/92; 71/94; 71/95

[58] Field of Search .................. 540/205, 460, 502; 544/254, 253, 279, 280

[56] References Cited

U.S. PATENT DOCUMENTS 3,887,557 6/1975 Minami et al. .................. 544/279
4,125,615 11/1978 Matsumoto .................. 544/279

Primary Examiner—Robert T. Bond
Attorney, Agent, or Firm—Sherman and Shalloway

[57] ABSTRACT

The present invention relates to novel 2-piperazinopyrimidine derivatives represented by the following general formula [I] which are useful as, for example, an active ingredient of herbicides

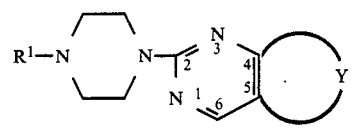

[I]

wherein $R^1$ is a hydrogen atom or an aralkyl group and Y is one of the groups represented by the following general formulas [II] to [VII]

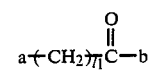

[II]

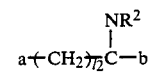

[III]

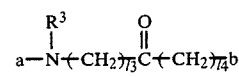

[IV]

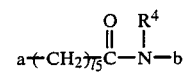

[V]

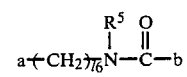

[VI]

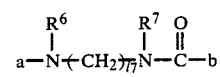

[VII]

(wherein a and b are positions to be bound to positions 4 and 5 of the pyrimidine ring of the formula [I], respectively; $l_1$ and $l_2$ each are an integer of 2 to 4; $l_3$ is 2 or 0; $l_4$ is 0 or 1, provided that $l_4$ is 0 when $l_3$ is 2 and $l_4$ is 1 when $l_3$ is 0; $l_5$ is 2 or 3; $l_6$ is 1 or 2; $l_7$ is 2 or 3; $R^2$ is a hydroxyl group or a toluenesulfonyloxy group; and $R^3$, $R^4$, $R^5$, $R^6$ and $R^7$ each are a hydrogen atom or a lower alkyl group).

3 Claims, No Drawings

2-PIPERAZINOPYRIMIDINE DERIVATIVES

TECHNICAL FIELD

This invention relates to novel 2-piperazinopyrimidine derivatives and a process for their production.

BACKGROUND ART

Compounds having a structure formed by the condensation of a nitrogen- or carbonyl-containing ring and a pyrimidine ring, for example, compounds having a pyridopyrimidine structure are known as mentioned in, for example, Chemical Abstracts, Vol. 90, 94893 (1979) and Vol. 97, 182350 (1982). However, these known compounds are greatly different in structure from the 2-piperazinopyrimidine derivatives of the present invention and their usefulness in agricultural applications are neither explained nor suggested in the above publications.

The present inventors conducted an extensive study on 2-piperazinopyrimidine derivatives. As a result, the inventors have succeeded in the synthesis of the novel 2-piperazinopyrimidine derivatives of the present invention greatly different in structure from the known compounds mentioned above and further have found that these novel compounds have an excellent herbicidal activity, and have completed the present invention.

DISCLOSURE OF THE INVENTION

The present invention provides 2-piperazinopyrimidine derivatives represented by the following general formula [I].

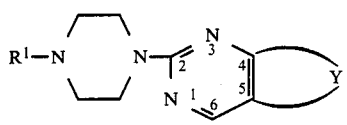

[I]

wherein $R^1$ is a hydrogen atom or an aralkyl group and Y is one of the groups represneted by the following general formulas [II] to [VII]

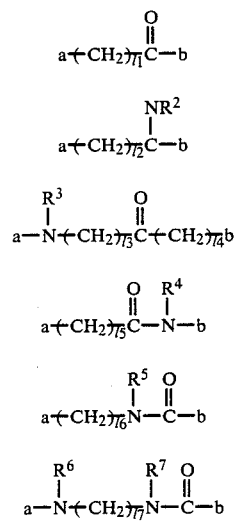

(wherein a and b are positions to be bound to positions 4 and 5 of the pyrimidine ring of the formula [I], respectively; $l_1$ and $l_2$ each are an integer of 2 to 4; $l_3$ is 2 or 0; $l_4$ is 0 or 1, provided that $l_4$ is 0 when $l_3$ is 2 and $l_4$ is 1 when $l_3$ is 0; $l_5$ is 2 or 3; $l_6$ is 1 or 2; $l_7$ 2 or 3; $R^2$ is a hydroxyl group or a toluenesulfonyloxy group; and $R^3$, $R^4$, $R^5$, $R^6$ and $R^7$ each are a hydrogen atom or a lower alkyl group).

As the arlkyl group of $R^1$ of the general formula [I], there can be mentioned a benzyl group, a diphenylmethyl group, a triphenylmethyl group, etc. Of these, a benzyl group is particularly preferred. Y of the general formula [I] is one of the groups represented by the general formulas [II] to [VII].

In the general formulas [II] and [III], $l_1$ and $l_2$ each are an integer of 2 to 4 and preferably 2 or 3. In the general formula [IV], $l_3$ is 0 or 2 and $l_4$ is 0 or 1, provided that $l_4$ is 1 when $l_3$ is 0 and $l_4$ is 0 when $l_3$ is 2. As the lower alkyl group of $R^3$, there can be mentioned, for example, alkyl groups of 1 to 4 carbon atoms such as methyl group, ethyl group, propyl group, isopropyl group, n-butyl group, isobutyl group, sec-butyl group, tert-butyl group and the like. Of these, an ethyl group is particularly preferred.

In the general formula [V], $l_5$ is 2 or 3 and preferably 3. $R^4$ can be a hydrogen atom or one of the lower alkyl groups mentioned with respect to $R^3$ and particularly preferably is a hydrogen atom or an ethyl group.

In the general formula [VI], $l_6$ is 1 or 2. $R^5$ is a hydrogen atom or one of the lower alkyl groups mentioned with respect to $R^3$ and particularly preferably is a hydrogen atom or an ethyl group.

In the general formula [VII], $l_7$ is 2 or 3 and preferably 2. $R^6$ and $R^7$ each are a hydrogen atom or a lower alkyl group. As the lower alkyl group, there can be mentioned those listed with respect to $R^3$ and an ethyl group is preferable.

The compounds of the present invention can take a free form as well as a salt form such as an acid addition salt or the like. Therefore, in the present invention, the 2-piperazinopyrimidine derivatives of the general formula [I] include their salts. These salts as well can be used as a herbicide. As the acid addition salts, there can be mentioned, for example, salts with a mineral acid such as hydrochloric acid, sulfuric acid, phosphoric acid or the like or with an organic acid such as acetic acid, maleic acid, citric acid or the like.

Examples of the present invention compounds are shown below. In the following formulas, Et is ethyl and $Pr^i$ is isopropyl.

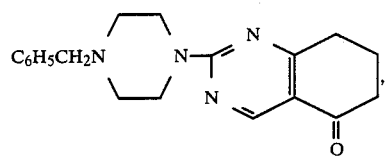

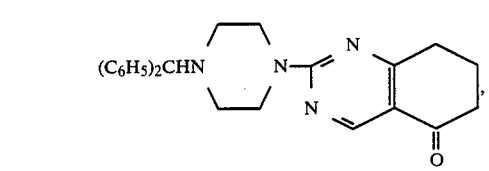

-continued

-continued

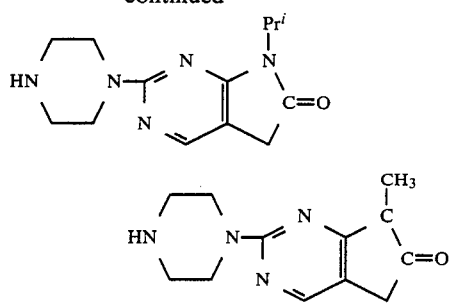

[PRODUCTION PROCESS NO. 1]

Of the presnet invention compounds of the general formula [I], those having the Y represented by the formula [II] can be produced according to the following process. For example, a compound ① wherein l₁ of the formula [II] is 3 and R¹ is a benzyl group, or a compound ⑥ wherein l₁ of the formula [II] is 3 and R¹ is a hydrogen atom can be produced as follows.

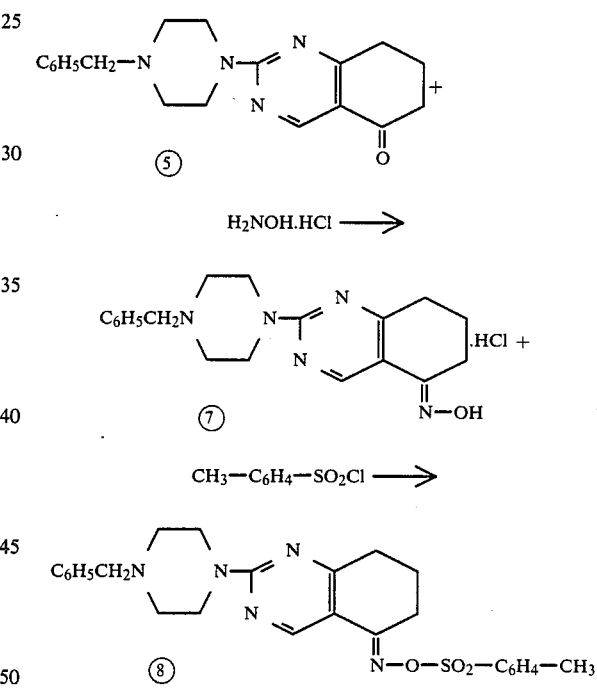

The starting material is a cycloalkene-1,3-dione or the like. Specifically, cyclopentane-1,3-dione or cyclohexane-1,3-dione ① is used. For example, 1 mole of the compound ① is mixed with about 2 mole of N,N-dimethylformamide dimethylacetal with ice-cooling and they are reacted for several hours at normal temperature to obtain a compound ③.

The compound ③ is reacted with a compound ④ for 1 to several hours in an alcohol medium such as methanol, ethanol, propanol or the like in the presence of a caustic alkali, with refluxing the alcohol medium, to obtain a compound ⑤. The compound ⑤ is subjected to hydrogenolysis to obtain a compound ⑥. Examples of the hydrogenolysis catalyst include Pd-C, Raney-Ni, Pt-C, PdO, etc. Examples of the reaction solvent include alcohols such as methanol, ethanol, isopropanol and the like; carboxylic acids such as formic acid, acetic acid, propionic acid and the like; and mixed solvents such as ethanol-formic acid, ethanol-acetic acid and the like. The reaction can be conducted, for example, at 10° to 100° C. for 0.1 to 10 hours with feeding hydrogen at normal pressure to 10 kg/cm².

[PRODUCTION PROCESS NO. 2]

Of the present invention compounds of the general formula [I], those having the Y represented by the general formula [III] can be produced by using, as the material, one of the compounds obtained according to the above Production Process No. 1, for example, the compound ⑤ or ⑥. When, for example, the compound ⑤ is used, the production is conducted as follows.

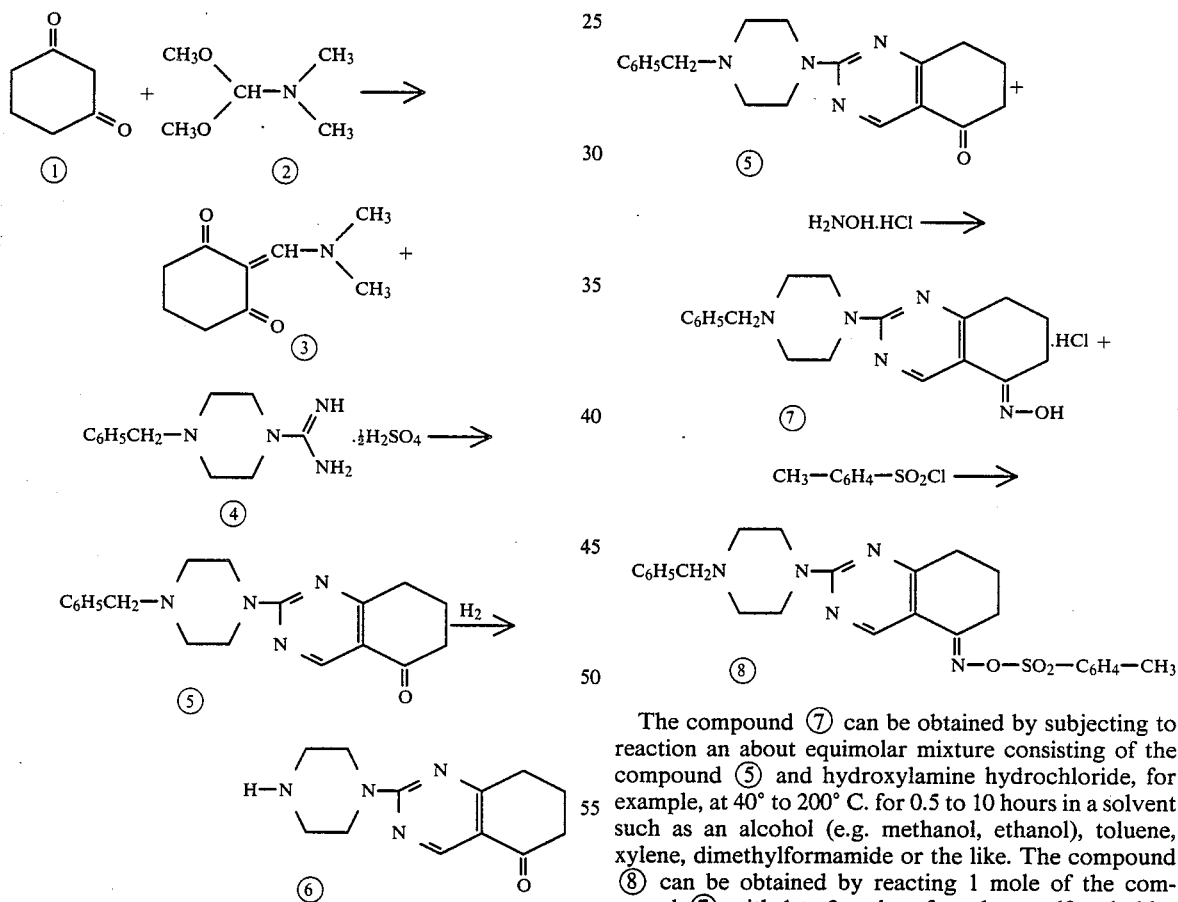

The compound ⑦ can be obtained by subjecting to reaction an about equimolar mixture consisting of the compound ⑤ and hydroxylamine hydrochloride, for example, at 40° to 200° C. for 0.5 to 10 hours in a solvent such as an alcohol (e.g. methanol, ethanol), toluene, xylene, dimethylformamide or the like. The compound ⑧ can be obtained by reacting 1 mole of the compound ⑦ with 1 to 2 moles of p-toluenesulfonyl chloride, for example, at 0° to 100° C. for 0.5 to 10 hours in a solvent such as water, acetone, in alcohol, toluene or their mixture. The essentially same production process as above can be applied to obtain compounds having l₁ and l₂ each of 2 or 4.

[PRODUCTION PROCESS NO. 3]

Of the present invention compounds of the general formula [I], those having the Y represented by the formula [IV], $l_3$ of 0 and $l_4$ of 1 and having, as $R^1$, a benzyl group can be produced as follows.

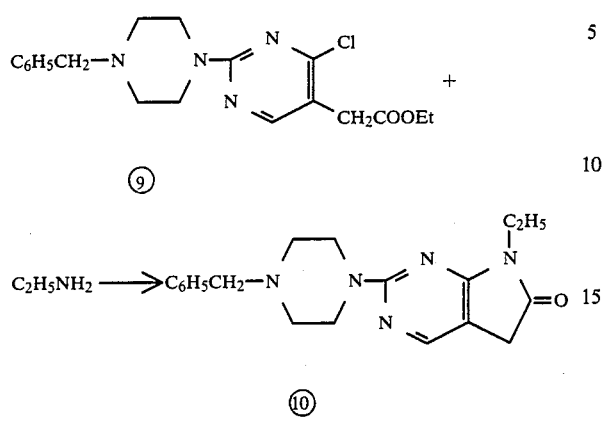

In the above case, a desired compound can be obtained by heating the compound ⑨ and an alkylamine corresponding to $R^3$ of the formula [IV] such as ethylamine, for example, at 100° to 140° C. for several hours in an alcohol medium such as isopropanol or the like. Compounds having the same Y, $l_3$ and $l_4$ as above but having, as $R^1$, a hydrogen atom can be obtained by subjecting a compound such as the compound ⑩ to hydrogenolysis in the same manner as mentioned in [Production Process No. 1].

[PRODUCTION PROCESS NO. 4]

Of the present invention compounds of the general formula [I], those having the Y represented by the formula [IV], $l_3$ of 2 and $l_4$ of 0 can be synthesized, for example, as follows from a known compound ⑪.

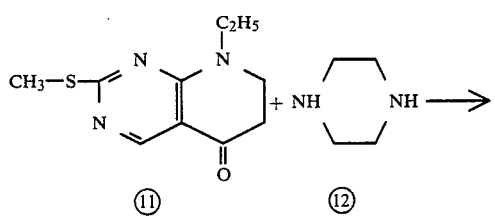

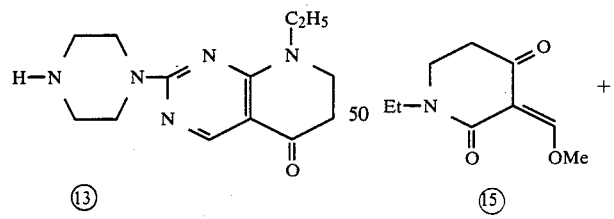

In the above case, 1 mole of the compound ⑪ and, for example, 2 to 3 moles of a compound ⑫ are reacted, for example, at 100° to 150° C. for 1 to several hours in a solvent such as dimethylsulfoxide, N,N-dimethylformamide, pyridine or the like. Compounds having the same Y, $l_3$ and $l_4$ as above but having, as $R^1$, an aralkyl group can be synthesized in the same manner as above by using a 1-aralkylpiperazine in place of the compound ⑫.

[PRODUCTION PROCESS NO. 5]

Of the present invention compounds of the general formula [I], those having the Y represented by the formula [V] can be synthesized, for example, according to the following reaction which is the rearrangement reaction of the compound ⑧ mentioned in [Production Process No. 2].

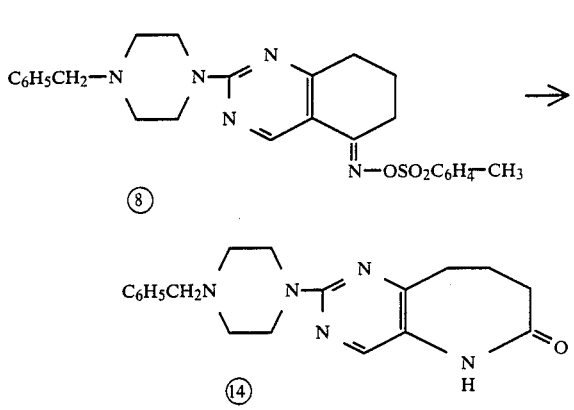

The compound ⑭ having, as $R^1$, an aralkyl group can be obtained by heating the corresponding compound ⑧ at, for example, 0° to 200° C., preferably 30° to 140° C. for, for example, 0.5 to 10 hours in a carboxylic acid (e.g. formic acid, acetic acid, propionic acid) or an alcohol (e.g. ethanol). Compounds having, as $R^4$, a lower alkyl group can be obtained by reacting a compound corresponding to the compound ⑭ with a lower alkyl bromide such as ethyl bromide in tetrahydrofuran or an alcohol in the presence of NaH, NaOEt, KOEt, $K_2CO_3$, $Na_2CO_3$, NaOH or KOH. This reaction can be conducted under conditions of, for example, 0° to 100° C. and 0.5 to 10 hours.

Compounds of the general formula [I] having a hydrogen atom as $R^1$ and the Y represented by the formula [V] can be obtained by subjecting the compound ⑭ to hydrogenolysis in the same manner as mentioned in [Production Process No. 1].

[PRODUCTION PROCESS NO. 6]

Those compounds of the genral formula [I] having the Y represented by the formula [VI] and $l_6$ of 2 can be produced according to the following reaction formula.

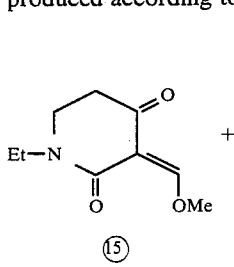

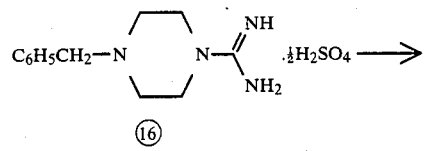

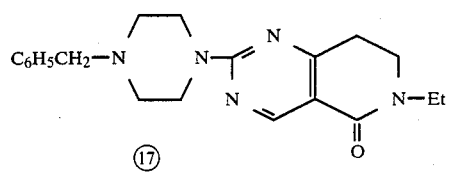

The above reaction can be conducted by, for example, heating the compound ⑮ and the compound 16 for 1 to several hours in an ethanol solvent in the presence of a base such as NaOH, KOH or the like, with refluxing ethanol. Incidentally, the compound ⑮ can be synthesized according to a method mentioned in Reference Examples 1 to 5 which appear later. Materials other than the compound ⑮, used for the production of compounds of the general formula [I] having the Y represented by the formula [VI] and $l_6$ of 1 can also be synthesized in the same manner. Compounds of the present invention having a hydrogen atom as $R^1$ and the Y represented by the formula [VI] can be produced by subjecting a compound such as the compound ⑰, having an aralkyl group as $R^1$ to the same hydrogenolysis as mentioned in [Production Process No. 1]. The present invention compound ⑰ can be produced also by hydrogenating the following compound

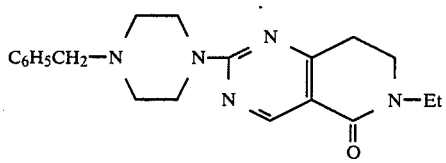

which is obtained according to "Pyridopyrimidine Derivatives and Process for Their Production" in the patent application (2) of Aug. 6, 1984 by the present applicant.

[PRODUCTION PROCESS NO. 7]

Compounds of the general formula [I] having the Y represented by the formula [VI] and $l_6$ of 1 can be produced also according to the following reaction formula.

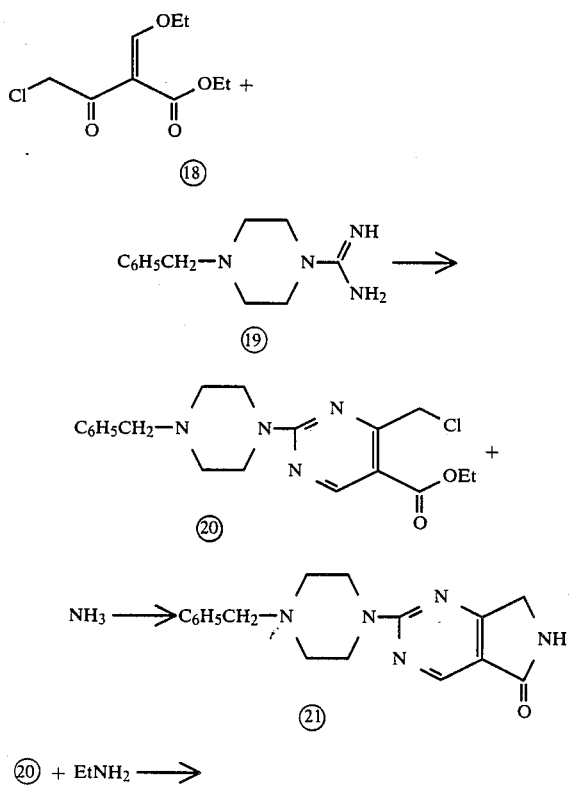

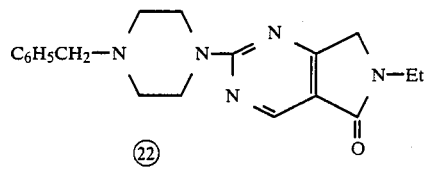

The compound ⑱ can be synthesized, for example, according to Reference Example 6 which appears later. The reaction between the compound ⑱ and the compound ⑲ can be conducted, for example, at 0° to 100° C. for 0.5 to 10 hours in a solvent such as water, methanol, ethanol, tetrahydrofuran, dimethylformamide or the like. The compound ㉑ and the compound ㉒ can be synthesized by reacting the compound ⑳ with ammonia and an amine having an alkyl group corresponding to $R^5$, respectively, that is, by reacting the materials, for example, at 0° to 150° C. for 0.5 to 20 hours in a solvent such as water, an alcohol, tetrahydrofuran, dimethylformamide, toluene, xylene or the like.

Compounds of the general formula [I] having a hydrogen atom as $R^1$ and the Y represented by the formula [VI] can be obtained by subjecting to hydrogenolysis a compound corresponding to the compound ㉑ or ㉒ in the same manner as mentioned in [Production Process No. 1].

[PRODUCTION PROCESS NO. 8]

Compounds of the general formula [I] having the Y represented by the formula [VII] can be obtained by, for example, reacting (1) a pyrimidiazepine derivative as obtained in Reference Example 9 which appears later and (2) a 1-aralkylpiperazine such as 1-benzylpiperazine or the like.

This reaction can be conducted at 140° to 170° C. for several tens of hours by using 1 mole of the former compound and 4 to 5 moles of the latter compound. Compounds of the general formula [I] having a hydrogen atom as $R^1$ and the Y represented by the formula [VII] can be produced by subjecting to hydrogenolysis corresponding compound having, as $R^1$, an aralkyl group, particularly, a benzyl group in the same manner as mentioned in [Production Process No. 1].

BEST MODE FOR CARRYING OUT THE INVENTION

The present invention compounds of the general formula [I] can specifically be produced as follows. These compounds can be utilized as a herbicidally active compound as shown later by the data on some of the compounds.

REFERENCE EXAMPLE 1

Ethyl 3-ethylaminopropionate 50 g (0.50 mole) of ethyl acrylate was dissolved in 500 ml of ethanol. To the resulting solution being stirred in an ice bath was added dropwise a mixed solution consisting of 36 g of a 70% aqueous ethylamine solution (containing 0.55 mole of ethylamine) and 100 ml of ethanol, in 3.5 hours. The reaction was continued for further 3 hours and then the solvent was distilled off. The resulting residue was subjected to vacuum distillation to obtain 50.5 g of a desired product with an yield of 70%.

Colorless liquid.

Boiling point: 65° C./10 mmHg.

Infrared absorption spectrum (neat, cm$^{-1}$) 3320 (broad), 1735.

$^1$H-NMR spectrum (CDCl$_3$ solution, δ ppm) 1.0–1.4 (6H, m), 2.4–3.0 (6H, m), 4.16 (2H, q, J=7.0 Hz).

REFERENCE EXAMPLE 2

Ethyl N-ethoxycarbonylacetyl-3-ethylaminopropionate

To a mixture consisting of 45 g (0.30 mole) of ethyl 3-ethylaminopropionate, 37.3 g (0.27 mole) of potassium carbonate, 250 ml of toluene and 250 ml of water being stirred in an ice bath was added dropwise 67.7 g (0.45 mole) of ethylmalonyl chloride in 0.5 hour. Stirring was continued for further 3 hours at room temperature and the reaction mixture was subjected to phase separation. The toluene layer obtained was washed with a 5% aqueous HCl solution, a saturated aqueous sodium bicarbonate solution and a saturated aqueous NaCl solution in this order and then dried with anhydrous magnesium sulfate. The resulting solution was subjected to vacuum distillation to remove toluene, whereby 64.3 g of a desired product was obtained with an yield of 83%.

Colorless liquid.

Infrared absorption spectrum (neat, cm$^{-1}$) 1735, 1648.

$^1$H-NMR spectrum, (CDCl$_3$ solution, δ ppm) 1.1–1.3 (6H), 2.64 (2H), 3.2–3.8 (6H), 4.0–4.2 (4H).

REFERENCE EXAMPLE 3

3-Carbethoxy-1-ethylpiperidine-2,4-dione 5.8 g of metallic sodium was added to 300 ml of ethanol and they were reacted to obtain an ethanol solution containing sodium ethoxide. To this solution was added 62.2 g of ethyl N-ethoxycarbonylacetyl-3-ethylaminopropionate, and they were refluxed for 4 hours and allowed to cool. Ethanol was distilled off. Thereto were added ethyl acetate and a dilute aqueous hydrochloric acid solution and the resulting mixture was shaken. The organic layer was separated, water-washed, dried and concentrated to obtain 36.3 g of 3-carboethoxy-1-ethylpiperidine-2,4-dione as an oily matter with an yield of 71%.

$^1$H-NMR spectrum (CDCl$_3$ solution, δ ppm) 1.28 (6H, m), 2.66 (2H, m), 3.44 (4H, m), 4.32 (2H, m).

REFERENCE EXAMPLE 4

1-Ethylpiperidine-2,4-dione 300 ml of a 10% aqueous hydrochloric acid solution was added to 36.0 g of 3-carboethoxy-1-ethylpiperidine-2,4-dione, and they were refluxed for 40 minutes and allowed to cool. The resulting mixture was subjected to extraction by chloroform. The resulting chloroform layer was water-washed, dried and concentrated to obtain 16.6 g of 1-ethylpiperidine-2,4-dione as a light yellow oily matter with an yield of 70%.

$^1$H-NMR spectrum (CDCl$_3$ solution, δ ppm) 1.20 (3H, t, J=7 Hz), 2.64 (2H, t, J=7 Hz), 3.36 (2H, s), 3.54 (4H, m).

REFERENCE EXAMPLE 5

1-Ethyl-3-methoxymethylenepiperidine-2,4-dione 11 g of methyl orthoformate and 20 ml of acetic anhydride were added to 8.3 g of 1-ethylpiperidine-2,4-dione, and they were refluxed for 7 hours and then allowed to cool. Excessive methyl orthoformate and acetic anhydride were removed by vacuum distillation. The resulting brown reside was subjected to vacuum distillation (0.5 mmHg, bath temperature of 200° to 250° C.) using a kugelrohr apparatus, whereby 2.7 g of 1-ethyl-3-methoxymethylenepiperidine-2,4-dione was obtained as a crystal with an yield of 25%. This crystal was recrystallized from a mixed solvent consisting of ethyl acetate and hexane to obtain a needle-like crystal of said compound.

$^1$H-NMR spectrum (CDCl$_3$ solution, δ ppm) 1.20 (3H, m), 2.64 (2H, t, J=7 Hz), 3.50 (4H, m), 4.12 (3H, s), 7.86 (1H, two s).

EXAMPLE 1

2-(4-Benzylpiperazino)-6-ethyl-5-oxo-5,6,7,8-tetrahydropyrido[4,3-d]pyrimidine (In the general formula [I], Y is [IV].)

1.56 g of 1-amidino-4-benzylpiperazine sulfate was added to an ethanol solution containing 0.23 g of sodium hydroxide. To the resulting suspension was added 1.07 g of 1-ethyl-3-methoxymethylenepiperidine-2,4-dione, and they were refluxed for 2 hours. Ethanol was distilled off. Then, water was added and extraction by chloroform was conducted. The chloroform layer was dried and concentrated to obtain 1.4 g of 2-(4-benzylpiperazino)-6-ethyl-5-oxo-5,6,7,8-tetrahydropyrido[4,3-d]pyrimidine with an yield of 69%.

Melting point: 128°–130° C.

$^1$H-NMR spectrum (CDCl$_3$ solution, δ ppm) 1.20 (3H, t, J=7 Hz), 2.50 (4H, m), 2,94 (2H, t, J=8 Hz), 3.55 (6H, m), 3.92 (4H, m), 7.32 (5H, m), 8.92 (1H, s).

EXAMPLE 2

6-Ethyl-5-oxo-2-piperazino-5,6,7,8-tetrahydropyrido[4,3-d]pyrimidine (In the general formula [I], Y is [VI].)

In 20 ml of ethanol was dissolved 0.70 g of 2-(4-benzylpiperazino)-6-ethyl-5-oxo-5,6,7,8-tetrahydropyrido[4,3-d]pyrimidine. Thereto was added 10% Pd-C, and the resulting mixture was stirred at 60° C. for 4 hours in a hydrogen atmosphere. After having been allowed to cool, the mixture was filtered to remove the catalyst and the filtrate was concentrated to obtain 0.50 g of 6-ethyl-5-oxo-2-piperazino-5,6,7,8-tetrahydropyrido[4,3-d]pyrimidine as a crystal with an yield of 96%. The crystal was purified by immersion using ethyl acetate.

Melting point: 205°–210° C.

$^1$H-NMR spectrum (CDCl$_3$ solution, δ ppm) 1.20 (3H, t, J=7 Hz), 3.00 (6H, m), 3.60 (4H, m), 3.94 (4H, m), 8.84 (1H, s).

REFERENCE EXAMPLE 6

Ethyl-4-chloro-2-ethoxymethyleneacetoacetate 10 g (60.7 mM) of ethyl 4-chloroacetoacetate, 18 g (121 mM) of ethyl orthoformate and 25 g (245 mM) of acetic anhydride were stirred at 110° C. for 3 hours. Then, excessive ethyl orthoformate and acetic anhydride were distilled off under vacuum and the residue was recrystallized from hexane to obtain 12.1 g of a needle-like crystal with an yield of 90%.

Melting point: 86.5° C.

$^1$H-NMR spectrum (CDCl$_3$ solution, δ ppm) 1.35 (3H, t, J=7 Hz), 1.44 (3H, t, J=7 Hz), 4.30 (2H, q, J=7 Hz), 4.33 (2H, q, J=7 Hz), 4.56 (2H, s), 7.88 (1H, s).

Infrared absorption spectrum (KBr tablet, cm$^{-1}$): 2900, 2830, 1686, 1670, 1575, 1250, 1018.

REFERENCE EXAMPLE 7

Ethyl-4-chloro-methyl-2-(4-benzylpiperazino)pyrimidine-5-carboxylate

A solution consisting of 15 ml of water and 1.5 g of NaOH was added to a suspension consisting of 9.7 g (36.4 mM) of 1-amidino-4-benzylpiperazine sulfate and 185 ml of tetrahydrofuran, to conduct neutralization.

Thereto was added dropwise at 20° C. a solution consisting of 200 ml of tetrahydrofuran and 8 g (36.4 mM) of ethyl 4-chloro-2-ethoxymethyleneacetoacetate, after which they were stirred at that temperature for 1 hour. Then, 300 ml of ether was added and water washing was conducted three times. The organic layer was dried with anhydrous MgSO$_4$. The solvent was distilled off under vacuum to obtain 11.8 g of a desired compound of light yellow color with an yield of 86.7%.

$^1$H-NMR spectrum (CDCl$_3$ solution, δ ppm) 1.37 (3H, t, J=7 Hz), 2.51 (4H, t, J=6 Hz), 3.75 (2H, s), 3.96 (4H, t, J=6 Hz), 4.34 (2H, q, J=7 Hz), 4.88 (2H, s), 7.32 (5H, s), 8.87 (1H, s)

Infrared absorption spectrum (neat, cm$^{-1}$): 2873, 2780, 1706, 1582, 1526, 1445, 1350, 1250, 1090, 1000, 742, 696.

EXAMPLE 3

2-(4-Benzylpiperazino)-5-oxo-5,6-dihydro(7H)pyrrolo[3,4-d]pyrimidine (In general formula [I], Y is [VI].)

2.25 g (6 mM) of ethyl 4-chloromethyl-2-(4-benzylpiperazino)pyrimidine-5-carboxylate was dissolved in 10 ml of ethanol. Thereto was added 10 ml of a 30% aqueous NH$_4$OH solution (containing 59 ml of NH$_4$OH) at 20° C., and the mixture was stirred for 12 hours. The reaction mixture was poured into a 10% aqueous NaHCO$_3$ solution, and extraction by CHCl$_3$ was conducted. The solvent was distilled off from the CHCl$_3$ layer and the resulting residue was recrystallized from toluene.

Yield: 0.70 g (38%).

Melting point: 172° C.

$^1$H-NMR spectrum (DMSO-d$_6$ solution, δ ppm) 2.45 (4H, t, J=6 Hz), 3.50 (2H, s), 3.83 (4H, t, J=6 Hz), 4.20 (2H, s), 7.30 (5H, s), 8.20 (1H, br. s), 8.57 (1H, s)

Infrared absorption spectrum (nujol, cm$^{-1}$): 2900, 1715, 1674, 1607, 1562, 1218, 1145, 730, 720.

EXAMPLE 4

2-Piperazino-5-oxo-5,6-dihydro(7H)pyrrolo[3,4-d]pyrimidine (In the general formula [I], Y is [VI].)

Hydrogen was bubbled through a mixture being heated at 60° C., consisting of 1.6 g (5.18 mM) of 2-(4-benzylpiperazino)-5-oxo-5,6-dihydro(7H)pyrrolo[4,3-d]pyrimidine, 0.16 g of 10% Pd-C and 30 ml of AcOH. One hour later, the solvent was distilled off. The residue was suspended in a 10% aqueous NaHCO$_3$ solution, and the insolubles were collected by filtration and dried to obtain 0.75 g of a desired compound as an oily substance with an yield of 66%.

$^1$H-NMR spectrum (DMSO-d$_6$ solution, δ ppm) 2.80 (4H, br. s), 3.24 (1H, br. s), 3.78 (4H, br. s), 4.23 (2H, s), 8.18 (1H, br. s), 8.58 (1H, s).

Infrared absorption spectrum (KBr tablet, cm$^{-1}$): 3210, 3100, 2920, 2880, 1700, 1612, 1260, 1150, 980.

EXAMPLE 5

6-Ethyl-2-(4-benzylpiperazino)-5-oxo-5,6-dihydro(7H)pyrrolo[3,4-d]pyrimidine (In the general formula [I], Y is [VI].)

1.0 g (2.7 mM) of ethyl 4-chloromethyl-2-(4-benzylpiperazino)pyrimidine-5-carboxylate was dissolved in 10 ml of ethanol. Thereto was added at 20° C. 5 g of a 70% aqueous ethylamine solution (containing 59 mM of ethylamine). The mixture was stirred at 20° C. for 2 hours and at 80° C. for 0.5 hour.

After completion of the reaction, the reaction mixture was poured into water and neutralized with a 10% aqueous NaHCO$_3$ solution. Then, extraction by ether was conducted. The organic layer was dried, after which the solvent was distilled off. The residue was recrystallized from a mixed solvent consisting of toluene and hexane to obtain 0.82 g of a desired compound with an yield of 91%.

Melting point: 159.2° C.

$^1$H-NMR spectrum (CDCl$_3$ solution, δ ppm) 1.22 (3H, t, J=7 Hz), 2.50 (4H, t, J=6 Hz), 3.55 (2H, s), 3.59 (2H, q, J=7 Hz), 3.93 (4H, t, J=6 Hz), 4.18 (2H, s), 7.32 (5H, s), 8.64 (1H, s).

Infrared absorption spectrum (nujol, cm$^{-1}$): 2900, 1666, 1624, 1566, 1280, 1148, 1000, 975, 795, 733.

By using methylamine or isopropylamine in place of ethylamine, the following two compounds were obtained:

6-Methyl-2-(4-benzylpiperazino)-5-oxo-5,6-dihydro-(7H)pyrrolo[3,4-d]pyrimidine (In the general formula [I], Y is [VI].)

Yield: 94%.

Melting point: 178°–179° C.

$^1$H-NMR spectrum (CDCl$_3$ solution, δ ppm) 2.52 (4H, m), 3.15 (3H, s), 3.58 (2H, s), 3.96 (4H, m), 4.20 (2H, s), 7.36 (5H, m), 8.65 (1H, s).

Infrared absorption spectrum (CHCl$_3$ solution, cm$^{-1}$): 1685, 1618, 1522, 1350

6-Isopropyl-2-(4-benzylpiperazino)-5-oxo-5,6-dihydro(7H)pyrrolo[3,4-d]pyrimidine (In the general formula [I], Y is [VI].)

Yield: 39%.

Melting point: 173°–174° C.

$^1$H-NMR spectrum (CDCl$_3$ solution, δ ppm) 1.25 (6H, d, J=7 Hz), 2.52 (4H, m), 3.58 (2H, s), 3.96 (4H, m), 4.16 (2H, s), 4.64 (1H, sept., J=7 Hz), 7.36 (5H, m), 8.66 (1H, s).

Infrared absorption spectrum (CHCl$_3$ solution, cm$^{-1}$): 1680, 1618, 1530, 1345.

EXAMPLE 6

6-Ethyl-2-piperazino-5-oxo-5,6-dihydro(7H)pyrrolo[3,4-d]pyrimidine (In the general formula [I], Y is [VI].)

To 20 ml of AcOH were added 1.5 g (4.45 mM) of 6-ethyl-2-(4-benzylpiperazino)-5-oxo-5,6-dihydro(7H)-pyrrolo[3,4-d]pyrimidine and 0.15 g of 10% Pd-C. Hydrogen was bubbled therethrough at 80° C. to conduct a reaction for 1 hour.

After completion of the reaction, Pd-C was removed by filtration and AcOH was distilled off. The residue was dissolved in chloroform and neutralized with a 10% aqueous NaHCO$_3$ solution. The organic layer was dried with MgSO$_4$ and the solvent was distilled off. The residue was purified according to silica gel chromatography. The yield was 0.50 g (45%).

Melting point: 58.5° C.

$^1$H-NMR spectrum (CDCl$_3$ solution, δ ppm) 1.24 (3H, t, J=7 Hz), 2.12 (1H, br. s), 2.95 (4H, br. s), 3.62 (2H, q, J=7 Hz), 3.92 (4H, br. s), 4.21 (2H, s), 8.66 (1H, s).

Infrared absorption spectrum (KBr tablet, cm$^{-1}$): 3480, 3300, 2900, 1650, 1618, 1520, 1438, 1236, 1160, 862.

In the similar manner, the following two compounds were obtained.

6-Methyl-2-piperazino-5-oxo-5,6-dihydro(7H)pyrrolo[3,4-d]pyrimidine (In the general formula [I], Y is [VI].)
Yield: 100%.
Melting point: 176°-177° C.

$^1$H-NMR spectrum (CDCl$_3$ solution, δ ppm) 2.98 (4H, m), 3.18 (3H, s), 3.96 (4H, m), 4.24 (2H, s), 8.70 (1H, s).

Infrared absorption spectrum (CHCl$_3$ solution, cm$^{-1}$): 1685, 1618, 1522, 1350.

6-Isopropyl-2-piperazino-5-oxo-5,6-dihydro(7H)pyrrolo[3,4-d]pyrimidine (In the general formula [I], Y is [VI].)
Yield: 96%.
Melting point: 161°-162° C.

$^1$H-NMR spectrum (CDCl$_3$ solution, δ ppm) 1.28 (6H, d, J=7 Hz), 2.96 (4H, m), 3.94 (4H, m), 4.18 (2H, s), 4.65 (1H, sept., J=7 Hz), 8.70 (1H, s).

Infrared absorption spectrum (CHCl$_3$ solution, cm$^{-1}$): 1680, 1618, 1520, 1345.

REFERENCE EXAMPLE 8

2-Dimethylaminomethylenecyclohexane-1,3-dione 11.9 g (100 mM) of N.N-dimethylformamide dimethylacetal was dropwise added to 5.6 g (50 mM) of cyclohexane-1,3-dione being stirred in an ice bath. The mixture was subjected to a reaction at 25° C. for 7 hours. The low-boiling substances in the reaction mixture were distilled off. The residue was recrystallized from ethyl acetatehexane to obtain 7.7 g of a desired compound as a yellow crystal with an yield of 92%.

Melting point: 106°-107° C.

$^1$H-NMR spectrum (CDCl$_3$ solution, δ ppm) 1.92 (2H, m), 2.47 (4H, m), 3.18 (3H, s), 3.40 (3H, s), 8.05 (1H, s).

EXAMPLE 7

2-(4-Benzylpiperazino)-5-oxo-5,6,7,8-tetrahydroquinazoline (In the general formula [I], Y is [II].)

To 60 ml of an ethanol suspension containing 10.73 g (40 mM) of 1-imidino-4-benzylpiperazine sulfate were added 80 ml of an ethanol solution containing 1.6 g (40 mM) of sodium hydroxide and then 6.69 g (40 mM) of 2-dimethylaminomethylenecyclohexane-1,3-dione. The mixture was refluxed for 4 hours and allowed to cool to room temperature. The solvent was distilled off. To the residue was added 100 ml of water, and extraction was conducted two times using 200 ml of ethyl acetate. The ethyl acetate layer was washed with a a saturated aqueous NaCl solution and dried with anhydrous magnesium sulfate. Ethyl acetate was distilled off under reduced pressure. The residue was purified according to silica gel chromatography [eluting solvent: ethyl acetate (3)/hexane(7)] to obtain 9.90 g of a desired compound as a light yellow crystal with an yield of 77%.

Melting point: 96°-97° C.

Infrared absorption spectrum (KBr tablet, cm$^{-1}$): 1665, 1590, 1530, 1515.

$^1$H-NMR spectrum (CDCl$_3$ solution, δ ppm) 2.08 (2H, m), 2.5 (6H, m), 2.80 (2H, m), 3.54 (2H, s), 3.96 (4H, m), 7.32 (5H, s), 8.83 (1H, s).

EXAMPLE 8

2-Piperazino-5-oxo-5,6,7,8-tetrahydroquinazoline (In the general formula [I], Y is [II].)

0.64 g (2 mM) of 2-(4-benzylpiperazino)-5-oxo-5,6,7,8-tetrahydroquinazoline was dissolved in 30 ml of ethanol and 10 ml of acetic acid. Thereto was added 64 mg of 10% Pd-C, and hydrogenation was conducted at 50° C. for 1 hour under normal pressure. The reaction mixture was cooled to room temperature. The catalyst was removed by filtration and the filtrate was subjected to vacuum distillation. The residue was recrystallized from ethyl acetate to obtain 0.42 g of a desired compound as a light yellow crystal with an yield of 90%.

Melting point: 161°-162° C.

Infrared absorption spectrum (KBr tablet, cm$^{-1}$) 3400 (broad), 1670, 1600, 1530.

$^1$H-NMR spectrum (CDCl$_3$ solution, δ ppm) 2.10 (2H, m), 2.60 (2H, m), 2.84 (2H, m), 3.06 (4H, m), 4.08 (4H, m), 8.85 (1H, s).

EXAMPLE 9

2-(4-Benzylpiperazino)-5,6,7,8-tetrahydro-5-hydroxyiminoquinazoline (In the general formula [I], Y is [III].)

To 30 ml of methanol were added 2.6 g (8.07 mM) of 2-(4-benzylpiperazino)-5-oxo-5,6,7,8-tetrahydroquinazoline and 0.67 g (9.64 mM) of hydroxylamine hydrochloride. The mixture was stirred at 60° C. for 2 hours and cooled to 20° C. The resulting precipitate was collected by filtration, whereby 2.85 g of a white solid was obtained with an yield of 95%.

Melting point: Above 300° C. (decomposed).

$^1$H-NMR spectrum (CDCl$_3$ solution, δ ppm) 1.80 (2H, m), 2.40-2.90 (8H, m), 3.58 (2H, s), 3.92 (4H, t, J=6 Hz), 7.34 (5H, s), 8.91 (1H, s).

Infrared absorption spectrum (KBr tablet, cm$^{-1}$) 3150, 2920, 2444, 1618, 1582, 1510, 1500, 1275, 1032, 955.

EXAMPLE 10

2-(4-Benzylpiperazino)-5,6,7,8-tetrahydro-5-(p-toluenesulfonyl)aminoquinazoline (In the general formula [I], Y is [III].)

2 g (5.35 mM) of 2-(4-benzylpiperazino)-5,6,7,8-tetrahydro-5-hydroxyiminoquinazoline, 1.6 g (8.4 mM) of p-toluenesulfonyl chloride and 0.7 g (11 mM) of KOH were added to a mixed solvent consisting of 10 ml of water and 30 ml of acetone. The mixture was stirred at 200° C. for 4 hours.

After completion of the reaction, the reaction mixture was poured into an aqueous NaCl solution. Extraction by ethyl acetate was conducted. The organic layer was evaporated to dryness. The residue was purified according to silica gel chromatography (etluting solvent: CHCl$_3$-ethanol) to obtain 1.5 g of a white solid with an yield of 59%.

Melting point: 180.6° C.

¹H-NMR spectrum 1.68–1.98 (2H, m), 2.44 (3H, s), 2.46–2.85 (8H, m), 3.57 (2H, s), 3.90 (4H, t, J=6 Hz), 7.26–7.40 (7H, m), 7.86 (1H, s), 7.95 (1H, s), 8.69 (1H, s).

Infrared absorption spectrum (KBr tablet, cm⁻¹) 2920, 1578, 1526, 1424, 1188, 1176, 1005, 992

EXAMPLE 11

2-(4-Benzylpiperazino)-6-oxo-6,7,8,9-tetrahydro(5H-)pyrimido[5,4-d]azepine (In the general formula [I], Y is [V].)

1.3 g (4 mM) of 2-(4-benzylpiperazino)-5,6,7,8-tetrahydro-5-(p-toluenesulfonyl)iminoquinazoline was dissolved in 30 ml of acetic acid. The solution was heated at 100° C. for 4 hours for reaction. After completion of the reaction, acetic acid was distilled off. The residue was dissolved in CHCl₃ and neutralized with a 10% aqueous NaHCO₃ solution. The solvent was distilled off and the residue was recrystallized from toluene to obtain 0.70 g of a white solid with an yield of 79%.

Melting point: 210.7° C.

¹H-NMR spectrum (CDCl₃ solution, δ ppm) 2.26–2.40 (4H, m), 2.49 (4H, t, J=6 Hz), 2.83 (2H, t, J=7 Hz), 3.55 (2H, s), 3.82 (4H, t, J=6 Hz), 7.32 (5H, s), 7.83 (1H, s), 7.94 (1H, s).

Infrared absorption spectrum (KBr tablet, cm⁻¹) 3150, 2900, 2830, 1660, 1595, 1346, 1010, 982.

EXAMPLE 12

5-Ethyl-2-(4-benzylpiperazino)-6-oxo-6,7,8,9-tetrahydro(5H)pyrimido[5,4-b]azepine (In the general formula [I], Y is [V].)

0.65 g (1.84 mM) of 2-(4-benzylpiperazino)-6-oxo-6,7,8,9-tetrahydro(5H)pyrimido[5,4-b]azepine and 0.15 g (3.75 mM) of 60% NaOH were added to 30 ml of tetrahydrofuran. The mixture was stirred at 20° C. for 30 minutes. Then, 3 g (27.8 mM) of ethyl bromide was added. The mixture was subjected to a reactin at 60° C. for 5 hours. After completion of the reaction, the solvent was distilled off and the residue was purified according to silica gel chromatography to obtain 0.65 g of a colorless oily compound with an yield of 92%.

¹H-NMR spectrum (CDCl₃ solution, δ ppm) 1.15 (3H, t, J=7 Hz), 2.16–2.38 (4H, m), 2.53 (4H, t, J=6 Hz), 2.74 (2H, t, J=5.5 Hz), 2.58 (2H, s), 3.80 (2H, q, J=7 Hz), 3.87 (4H, t, J=6 Hz), 7.35 (5H, s), 8.13 (1H, s).

Infrared absorption spectrum (KBr tablet, cm⁻¹) 2920, 1657, 1589, 1444, 1250, 1000, 980.

EXAMPLE 13

5-Ethyl-2-piperazino-6-oxo-6,7,8,9-tetrahydro-(5H)pyrimido[5,4-b]azepine (In the general formula [I], Y is [V].)

0.6 g (2.18 mM) of 5-ethyl-2-(4-benzylpiperazino)-6-oxo-6,7,8,9-tetrahydro(5H)pyrimido[5,4-b]azepine and 0.06 g of 10% Pd-C were added to a mixed solvent consisting of 30 ml of acetic acid and 10 ml of ethanol. The mixture was subjected to a reaction at 100° C. for 4 hours with bubbling hydrogen through the mixture. Then, Pd-C was removed by filtration and the filtrate was evaporated to dryness to obtain 0.5 g of a light yellow oily compound with an yield of 100%.

¹H-NMR spectrum (CDCl₃ solution, δ ppm) 1.16 (3H, t, J=7 Hz), 2.21–2.40 (4H, m), 2.75 (2H, t, J=5.5 Hz), 2.96 (4H, t, J=6 Hz), 3.70–4.05 (6H, m).

Infrared absorption spectrum (neat, cm⁻¹) 3460, 3300, 2940, 1650, 1595, 1445, 1128, 984.

In the similar manner, the following compound was obtained as follows.

2-Piperazino-6-oxo-6,7,8,9-tetrahydro(5H-)pyrimido[5,4-b]azepine (In the general formula [I], Y is [V].)

0.1 g (0.3 mM) of 2-(4-benzylpiperazino)-6-oxo-6,7,8,9-tetrahydro(5H)pyrimido[5,4-b]azepine and 0.01 g of 10% Pd-C were added to 20 ml of ethanol. The mixture was subjected to a reaction at 50° C. for 4 hours in a hydrogen atmosphere. Then, Pd-C was removed by filtration and the filtrate was evaporated to dryness to obtain 0.074 g of a white crystal quantitatively.

Melting point: 175°–178° C.

¹H-NMR spectrum (CDCl₃ solution, δ ppm) 2.2–2.5 (4H, m), 2.7–3.0 (2H, m), 2.94 (4H, t, J=4.5 Hz), 3.81 (4H, t, J=4.5 Hz), 7.00 (1H, br. s), 7.98 (1H, s).

Infrared absorption spectrum (nujol, cm⁻¹) 1685, 1600, 1505, 1350, 1235.

EXAMPLE 14

2-(4-Benzylpiperazino)-5,6-dihydro-7-ethyl-6-oxo(7H-)pyrrolo[2,3-d]pyrimidine (In the general formula [I], Y is [IV].)

In a pressure vessel was placed a mixture consisting of 1.41 g (3.76 mM) of ethyl 2-(4-benzylpiperazino)-4-chloropyrimidine-5-acetate, 5 ml of ethylamine and 20 ml of isopropanol. The mixture was heated for 2 hours at 120° C. Then, the solvent was removed under reduced pressure. Water was added and extraction by chloroform was conducted. The organic layer was dried with MgSO₄ and concentrated. The residue was purified according to silica gel column chromatography to obtain 0.58 g of the captioned compound with an yield of 46%.

Melting point: 110°–113° C.

Infrared absorption spectrum (CHCH₃ solution, cm⁻¹) 1725, 1620, 1570.

¹H-NMR spectrum (CDCl₃ solution, δ ppm) 1.25 (3H, t, J=7.0 Hz), 2.49 (4H, t, J=5.2 Hz), 3.37 (2H, s), 3.54 (2H, s), 3.75 (2H, q, J=7.2 Hz), 3.83 (4H, t, J=5.2 Hz), 7.31 (5H, s), 7.89 (1H, s).

Using methylamine or isopropylamine in place of ethylamine, the following two compounds were obtained.

2-(4-Benzylpiperazino)-5,6-dihydro-7-isopropyl-6-oxo(7H)pyrrolo[2,3-d]pyrimidine (In the general formula [I], Y is [IV].)
Yield: 36%.
Melting point: 125°–127° C.

¹H-NMR spectrum (CDCl₃ solution, δ ppm) 1.48 (6H, d, J=7 Hz), 2.50 (4H, m), 3.36 (2H, s), 3.56 (2H, s), 3.82 (4H, m), 4.62 (1H, sept., J=7 Hz), 7.33 (5H, m), 7.89 (1H, s).

Infrared absorption spectrum (KBr tablet, cm⁻¹) 1730, 1620, 1580, 1440, 1220, 1100.

2-(4-Benzylpiperazino)-5,6-dihydro-7-methyl-6-oxo(7H)pyrrolo[2,3-d]pyrimidine (In the general formula [I], Y is [IV].)
Yield: 72%.
Melting point: 172°–174° C.

¹H-NMR spectrum (CDCl₃ solution, δ ppm) 2.50 (4H, m), 3.18 (3H, m), 3.40 (2H, s), 3.54 (2H, s), 3.84 (4H, m), 7.34 (5H, m), 7.90 (1H, s).

Infrared absorption spectrum (KBr tablet, cm$^{-1}$) 1735, 1630, 1575, 1520, 1480, 1340, 1245.

EXAMPLE 15

5,6-Dihydro-7-ethyl-6-oxo-2-piperazino(7H)pyrrolo[2,3-d]pyrimidine (In the general formula [I], Y is [IV].)
0.54 g (1.60 mM) of 2-(4-benzylpiperazino)-5,6-dihydro-7-ethyl-6-oxo(7H)pyrrolo[2,3-d]pyrimidine was subjected to hydrogenation at normal pressure in the presence of 0.1 g of 10% Pd-C in 15 ml of an ethanol solvent containing 0.12 ml of formic acid. Refluxing was conducted for 4.5 hours. The catalyst was removed by filtration and ethanol was distilled off under reduced pressure. An aqueous sodium carbonate solution was added and extraction by chloroform was conducted. The organic layer was dried with MgSO$_4$ and concentrated to obtain 0.36 g of the captioned compound as an oily product with an yield of 91%.

$^1$H-NMR spectrum (CDCl$_3$ solution, δ ppm) 1.27 (3H, t, J=7.0 Hz), 2.02 (1H, br. s), 2.92 (4H, t, J=5.2 Hz), 3.40 (2H, s), 3.80 (6H, m), 7.91 (1H, s).

In the similar manner, the following two compounds were obtained.

5,6-Dihydro-7-isopropyl-6-oxo-2-piperazino(7H)pyrrolo[2,3-d]pyrimidine (In the general formula [I], Y is [IV].)
Yield: 83%.
Melting point: 113°–115° C.
$^1$H-NMR spectrum (CdCl$_3$ solution, δ ppm) 1.52 (6H, d, J=7 Hz), 2.08 (1H, brs), 2.93 (4H, m), 3.40 (2H, s), 3.80 (4H, m), 4.65 (1H, sept., J=7 Hz), 7.47 (1H, s), 7.93 (1H, s).

Infrared absorption spectrum (neat, cm$^{-1}$) 3330, 1725, 1622, 1575, 1440, 1220, 1110.

5,6-Dihydro-7-methyl-6-oxo-2-piperazino(7H)pyrrolo[2,3-d]pyrimidine (In the general formula [I], Y is [IV].)
Yield: 70%.
Melting point: 145°–147° C.
$^1$H-NMR spectrum (CDCl$_3$ solution, δ ppm) 1.86 (1H, brs), 2.94 (4H, m), 3.21 (3H, s), 3.43 (2H, s), 3.82 (4H, m), 7.93 (1H, s).

Infrared absorption spectrum (KBr tablet, cm$^{-1}$) 3340, 1738, 1630, 1580, 1450, 1105.

EXAMPLE 16

8-Ethyl-5-oxo-2-piperazino-5,6,7,8-tetrahydropyrido[2,3-d]pyrimidine (In the general formula [I], Y is [IV].)
A mixture consisting of 2.5 g (11.3 mM) of 8-ethyl-5-oxo-2-methylthio-5,6,7,8-tetrahydropyrido[2,3-d]pyrimidine (synthesized according to the process described in Japanese Patent Laid-open Publication No. 18600/1978), 2.93 g (34.0 mM) of anhydrous piperazine and 20 ml of dimethylsulfoxide was heated at 120° C. for 3.5 hours and successively at 140° C. for 6.5 hours. Dimethylsulfoxide was distilled off under reduced pressure for concentration. Water was added to the residue and extraction by chloroform was conducted. The organic layer was dried with MgSO$_4$ and concentrated to obtain 3.08 g of the captioned compound as an oily product with an yield of 90%.

$^1$H-NMR spectrum (CDCl$_3$ solution, δ ppm) 1.20 (3H, t, J=7.2 Hz), 1.77 (1H, s), 2.61 (2H, dd, J=6.6, 6.7 Hz), 2.90 (4H, m), 3.59 (4H, m), 3.88 (4H, m), 8.59 (1H, s).

REFERENCE EXAMPLE 9

6,9-Dimethyl-2-methylthio-5-oxo-5,6,7,8-tetrahydro(9H)pyrimido[4,5-e]diazepine

A solution consisting of 50 ml of ethanol and 5.0 g (21.5 mM) of ethyl 4-chloro-2-methylthio-pyrimidine-5-carboxylate was added dropwise in 50 minutes to a mixture consisting of 4.58 ml (43.0 mM) of N,N'-dimethylethylenediamine, 150 ml of ethanol and 2.51 g of Na$_2$CO$_3$. Refluxing was conducted for 13 hours. Ethanol was distilled off. Water was added to the residue and extraction by chloroform was conducted. The organic layer was dried and concentrated. The residue was purified according to silica gel column chromatography to obtain 3.55 g of the captioned compound with an yield of 69%.

Melting point: 153°–155° C.
$^1$H-NMR spectrum (CDCl$_3$ solution, δ ppm) 2.52 (3H, s), 3.13 (3H, s), 3.23 (3H, s), 3.63 (4H, AB quart.), 8.72 (1H, s).

EXAMPLE 17

6,9-Dimethyl-2-(4-benzylpiperazino)-5-oxo-5,6,7,8-tetrahydro(9H)pyrimido[4,5-e]diazepine (In the general formula [I], Y is [VII].)
1.3 g (5.46 mM) of 6,9-dimethyl-2-methylthio-5-oxo-5,6,7,8-tetrahydro(9H)pyrimido[4,5-e]diazepine and 4 g (22.69 mM) of 1-benzylpiperazin were stirred at 140° to 170° C. for 28 hours. After the mixture had been cooled, ethyl acetate was added thereto and the insolubles were removed by filtration. The filtrate was concentrated and purified according to column chromatography to obtain 0.2 g of an reddish brown oil with an yield of 10%.

$^1$H-NMR spectrum (CDCl$_3$ solution, δ ppm) 2.47 (4H, m), 3.11 (3H, s), 3.12 (3H, s), 3.55 (6H, m), 3.84 (4H, m), 7.32 (5H, m), 8.72 (1H, s).

EXAMPLE 18

6,9-Dimethyl-2-piperazino-5-oxo-5,6,7,8-tetrahydro(9H)pyrimido[4,5-e]diazepine (In the general formula [I], Y is [VII].)
In 10 ml of ethanol was dissolved 0.2 g (0.55 mM) of 6,9-dimethyl-2-(4-benzylpiperazino)-5-oxo-5,6,7,8-tetrahydro(9H)pyrimido[4,5-e]diazepine. Thereto was added 20 mg of 10% Pd-C, and refluxing was conducted for 2 hours at normal pressure to effect hydrogenation. After the mixture had been cooled to room temperature, the catalyst was removed by filtration and the filtrate was subjected to vacuum distillation. The residue was purified according to column chromatography to obtain 0.1 g of a desired compound with an yield of 67%.

$^1$H-NMR spectrum (CDCl$_3$ solution, δ ppm) 3.59 (6H, s), 3.27 (4H, m), 3.62 (4H, brs), 4.20 (4H, m), 8.70 (1H, s).

EXAMPLE OF COMPOUNDING AS HERBICIDE

Next, an example of compound of a herbicide using the present invention compound will be explained. The figures herein indicate % by weight. Example of compounding (wettable powder)
Present invention compound: 10%
Sodium salt of a higher alcohol sulfate: 3%

Kaolin: 87%

The above mixture was homogeneously blended and ground to use as a wettable powder.

TEST FOR THE HERBICIDAL EFFECT WHEN APPLIED BEFORE GERMINATION

A garden soil was packed in a ceramic pot having an inside diameter of 9 cm. *Amaranthus retroflexus L.* and *Cyperus Iria L.* were sowed therein. Successively, a dispersion consisting of 20 liters of water and 300 g of a wettable power containing a particular compound of the present invention was sprayed on the entire surface of the soil from above the pot using a small sprayer. (20 liters and 300 g are the amounts per one are of the soil area to be sprayed.) After this spraying, the pot was placed in a greenhouse for 21 days to examine the herbicidal effect of the compound. The following evaluation criterion was used.

HERBICIDAL EFFECT

5: Withered completely.
4: Herbicidal effect is high.
3: Herbicidal effect is medium.
2: Herbicidal effect is low.
1: Herbicidal effect is very slight.
0: No effect (normal).

The test results are shown in the following table.

TABLE

| Test compound | Amaranthus retroflexus L. | Cyperus Iria L. |
|---|---|---|
| Compound of Example 1 | 3 | 3 |
| Compound of Example 2 | 3 | 3 |
| Compound of Example 4 | 4 | 3 |
| Compound of Example 6 | 3 | 3 |
| Compound of Example 9 | 3 | 4 |
| Compound of Example 11 | 3 | 3 |
| Compound of Example 16 | 4 | 3 |

INDUSTRIAL APPLICABILITY

The present invention compounds have an excellent herbicidal activity and can be used as a herbicide for paddies and gardens. These compounds are particularly effective for paddy weeds such as *Echinochloa crus-galli L. Beauv. gar crusgalli, Cyperus difformis L., Monochoria vaginalis Presl, Scirpus juncoides Roxb. var. Hotarui Ohwi* and *Alisma canaliculatum A. Br. et Bouche,* as well as for garden weeds such as *Panicum Crus-galli L. var. frumentaceum Trin., Digitaria adscendens Henr., Polygonum nodosum Pers., Amaranthus retroflexus L., Cyperus Iria L.* and *Chenopodium album L. var. centrorubrum Makino.*

In using as a herbicide, the present invention compounds can be diluted to an appropriate concentration as they are or after having been mixed with a carrier, a surfactant, a dispersing agent, an auxiliary chemical, etc. to prepare a wettable powder, an emulsion, a granular, a fine granular or the like and then can be sprayed or directly applied.

What is claimed is:

1. A 2-piperazinopyrimidine derivative represented by the general formula [I]

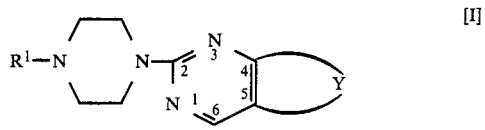

wherein $R^1$ is a hydrogen atom or an aralkyl group and Y is one of the groups represented by the following general formulas [II] to [VII]

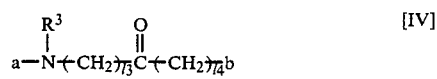

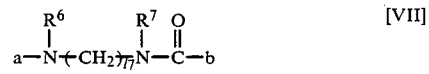

(wherein a and b are positions to be bound to 4 and 5 positions of the pyrimidine ring of the formula [I], respectively; $l_1$ and $l_2$ each are an integer of 2 to 4; $l_3$ is 2 or 0; $l_4$ is 0 or 1, provided that $l_4$ is 0 when $l_3$ is 2 and $l_4$ is 1 when $l_3$ is 0; $l_5$ is 2 or 3; $l_6$ is 1 or 2; $l_7$ is 2 or 3; $R^2$ is a hydroxyl group or a toluenesulfonyloxy group; and $R^3$, $R^4$, $R^5$, $R^6$ and $R^7$ each are a hydrogen atom or a lower alkyl group).

2. A 2-piperazinopyrimidine derivative according to claim 1, wherein the aralkyl group of $R^1$ is a benzyl group, a diphenylmethyl group or a triphenylmethyl group.

3. A 2-piperazinopyrimidine derivative according to claim 1, wherein $R^3$, $R^4$, $R^5$, $R^6$ and $R^7$ are a hydrogen atom or an alkyl group of 1 to 4 carbon atoms.

* * * * *